(12) United States Patent
Munson et al.

(10) Patent No.: US 9,220,682 B2
(45) Date of Patent: Dec. 29, 2015

(54) NANOCARRIER THERAPY FOR TREATING INVASIVE TUMORS

(75) Inventors: Jennifer M. Munson, Atlanta, GA (US); Ravi V. Bellamkonda, Marietta, GA (US); Jack L. Arbiser, Atlanta, GA (US)

(73) Assignees: Emory University, Atlanta, GA (US); Georgia Tech Research Corporation, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 1060 days.

(21) Appl. No.: 13/263,257

(22) PCT Filed: Apr. 21, 2010

(86) PCT No.: PCT/US2010/031914
§ 371 (c)(1),
(2), (4) Date: Nov. 4, 2011

(87) PCT Pub. No.: WO2010/124004
PCT Pub. Date: Oct. 28, 2010

(65) Prior Publication Data
US 2012/0052115 A1    Mar. 1, 2012

Related U.S. Application Data

(60) Provisional application No. 61/171,745, filed on Apr. 22, 2009.

(51) Int. Cl.
*A61K 9/127* (2006.01)
*A61K 9/00* (2006.01)

(52) U.S. Cl.
CPC .............. *A61K 9/1271* (2013.01); *A61K 9/0019* (2013.01)

(58) Field of Classification Search
CPC ........................................................ A61K 9/127
USPC ........................................................ 424/450
See application file for complete search history.

(56) References Cited

U.S. PATENT DOCUMENTS 3,760,007 A    9/1973    Steinman
6,331,564 B1   12/2001   Brugnara et al.
(Continued)

FOREIGN PATENT DOCUMENTS

WO    2008038291 A1    4/2008
WO    2009088838 A2    7/2009
WO    2010124004 A2    10/2010

OTHER PUBLICATIONS

Klingenberg, M., et al in Mol Cancer Ther. Apr. 13, 2014 (4), pp. 833-841.*

(Continued)

*Primary Examiner* — Gollamudi Kishore
(74) *Attorney, Agent, or Firm* — Meunier Carlin & Curfman LLC

(57) ABSTRACT

Liposomes of a size of less than 200 nanometers target tumors and preferentially deliver imipramine blue to tumors, including brain tumors such as gliomas. The imipramine blue decreases the invasiveness of the tumors, and inhibits tumor metastasis. The liposomes include cholesterol and chemically pure phospholipids that are essentially neutral and contain saturated fatty acids of between 16 and 18 carbon atoms, such as distearoylphosphatidyl choline, and can also include one or more pegylated phospholipids, such as DSPE-PEG.

8 Claims, 12 Drawing Sheets

(56) References Cited

U.S. PATENT DOCUMENTS

| | | |
|---|---|---|
| 8,435,979 B2 | 5/2013 | Arbiser |
| 2002/0123531 A1 | 9/2002 | Indig et al. |
| 2006/0165744 A1 | 7/2006 | Jamil et al. |
| 2007/0098802 A1 | 5/2007 | Farr et al. |
| 2007/0149479 A1 | 6/2007 | Fischer et al. |
| 2009/0176745 A1 | 7/2009 | Arbiser |
| 2010/0160296 A1 | 6/2010 | Arbiser |

OTHER PUBLICATIONS

International Search report issued in corresponding PCT Application No. PCT/US2010/031914, dated Dec. 22, 2010, 3 pgs.

Extended European Search report issued in corresponding EP Application No. 10767710.6, dated Mar. 13, 2014, 4 pgs.

Funding et al. Mitogen- and Stress-Activated Protein Kinase IIs Activated in Lesional Psoriatic Epidermis and Regulates the Expression of Pro-Inflammatory Cytokines, Journal of Investigative Dermatology (2006) 126, 1784-1791.

Lewis et al. "Effect of dye aggregation on triarylmethane-mediated photoinduced damage of hexokinase and DNA", Journal of Photochemistry and Photobiology, 2002, pp. 139-148, vol. 67.

Munson et al. Anti-Invasive Adjuvant Therapy with Imipramine Blue Enhances Chemotherapeutic Efficacy Against Glioma, Sci Transl Med 4, 127ra36 (2012).

Vippagunta et al. Advanced Drug Delivery Reviews, 2001, vol. 48, pp. 3-26.

* cited by examiner

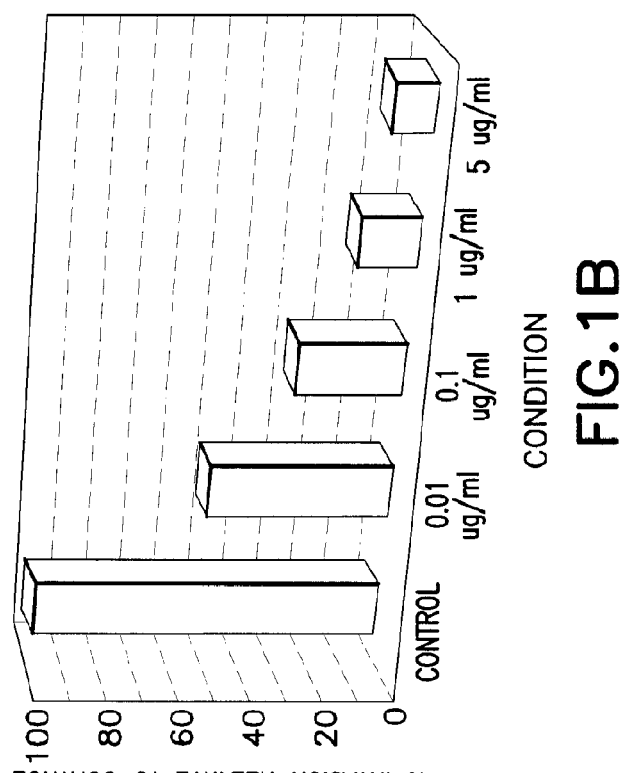
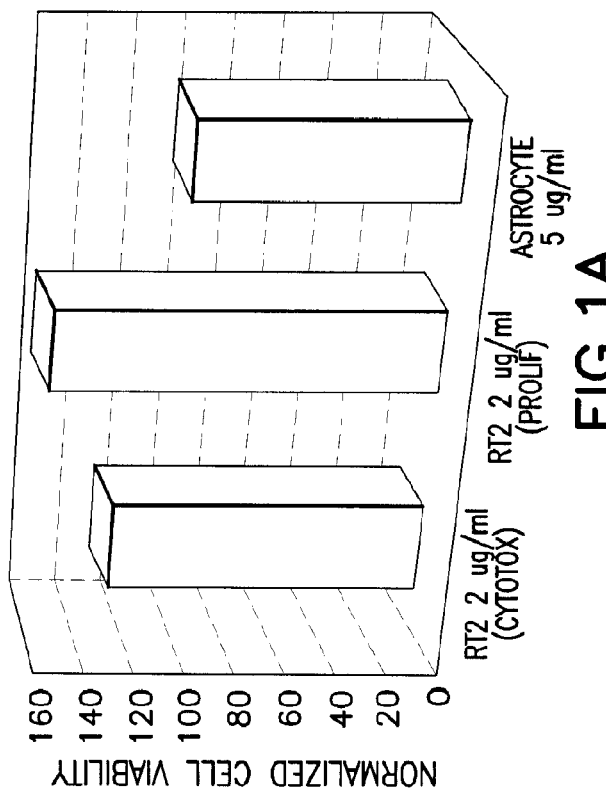

US 9,220,682 B2

NANOCARRIER THERAPY FOR TREATING INVASIVE TUMORS

CROSS REFERENCE TO RELATED APPLICATIONS

This application is a national phase application of International Patent Application PCT/US2010/031914 filed 21 Apr. 2010, which claims priority to U.S. Provisional Application Ser. No. 61/171,745 filed 22 Apr. 2009, which applications are hereby incorporated by this reference in their entireties.

FIELD OF THE INVENTION

This invention relates in general to the field of anti-cancer therapeutics, and more particularly, to the use of liposomes in the diagnosis and treatment of invasive tumors such as gliomas.

BACKGROUND OF THE INVENTION

Invasiveness of brain tumors is a major reason for poor prognosis after diagnosis. Unfortunately, there is a lack of available chemotherapeutic agents that negatively impact invasive gliomas. Additionally, gliomas present a difficult drug delivery paradigm due to the difficulty in transporting drugs across the blood-brain barrier.

Malignant glioma, also known as glioblastoma multiforme (GBM), is a highly infiltrative form of brain tumor with a five-year survival rate of 2%, characterized by diffuse cell spread within the tumor and into the surrounding brain creating an ill-defined tumor border. Primary treatment options for include surgical final IB concentration of 7-8 mg/ml resection, radiation, and chemotherapy. The rate of recurrence is high, and the average survival time post resection surgery is 18 months.

Novel therapeutics against cancer include more specific agents to attributes of tumor behavior including anti-angiogenics, antihypoxics, and anti-invasives. Several anti-invasive agents have shown promise in vitro for stopping tumor invasion and metastasis. These agents have not been tested in vivo due to limitations in delivery and dose accumulation at distant tumor sites.

It would be advantageous to provide new drugs and drug delivery systems to target glioma invasion in vivo. The present invention provides such compositions, and methods for their use.

SUMMARY OF THE INVENTION

Compositions and methods for treating cancer, particularly cancer characterized by the presence of invasive tumors, are disclosed. Although the compositions can be used generally to treat a variety of cancers, in one embodiment, they are used specifically to treat brain tumors, and, more specifically, to treat invasive gliomas.

The compositions include imipramine blue, or a pharmaceutically acceptable salt or prodrug thereof, in a liposome appropriately sized and formulated to cross the blood-brain barrier. In one embodiment, the liposomes include a pegylated phospholipid in a sufficient amount to increase the circulating half-life of the liposomes, to increase the amount of the encapsulated imipramine blue that can be administered.

The liposomes (preferably unilamellar vesicles) have a size less than 200 nm as measured by dynamic light scattering, and preferably characterized by being comprised of chemically pure synthetic phospholipids, most preferably having aliphatic side chains of a length of at least 16 carbons, and containing imipramine blue, or a pharmaceutically acceptable salt thereof, sufficient to preferentially deliver (i.e., target) a quantity of the imipramine blue to the tumor. Vesicle diameter can be measured, for example, by dynamic light scattering using a helium-neon 100 mW NEC gas laser and a Malvern K7027 correlator, ideally with at least two or three measurements made for each for each size determination.

The expression "chemically pure phospholipids" is meant to define phospholipids which are essentially free of deleterious detergent moieties and impurities which cause aggregation of small unilamellar vesicles (SUVs) formed therefrom, and which are more than 97% pure.

Preferably, the liposomes have a diameter predominantly of from about 50 to about 160 nm, are essentially neutral in charge, and incorporate phospholipids having a side chain length of from 16 to 18 carbon atoms. More preferably, the liposomes are prepared from distearoyl phosphatidylcholine (DSPC) and include cholesterol (most preferably in an amount of from 10 to 50% of total lipid) as a vesicle stabilizer. Most preferably, the liposomes further comprise a pegylated phospholipid, such as DSPE-PEG.

The method involves introducing into a patient's bloodstream an amount of liposomes, of a size of less than 200 nm (preferably unilamellar vesicles) and preferably characterized by being comprised of chemically pure synthetic phospholipids, most preferably having aliphatic side chains of a length of at least 16 carbons, and containing imipramine blue, or a pharmaceutically acceptable salt or prodrug thereof, sufficient to preferentially deliver (i.e., target) a quantity of the imipramine blue to the tumor.

While not wishing to be bound by any particular theory as to the targeting of the liposomes to tumors, it appears that the liposomes pass through capillaries with increased permeability (increased pore size) and can preferentially penetrate tumor tissue, relative to normal tissue. With respect to treating brain tumors, it is relevant to note that the liposomes cross the blood brain barrier and deliver the imipramine blue to the brain. It is also believed that the imipramine blue, once administered to the tumor site, inhibits both tumor invasion and tumor metastasis. However, imipramine blue can be administered at dosages at which it is anti-invasive, but not cytotoxic or anti-proliferative, and provides a dose-dependent anti-invasive response against malignant gliomas. At elevated dosages, imipramine blue is both anti-invasive and cytotoxic.

The imipramine blue can be combined with other conventional anti-tumor agents, as well as diagnostic agents. Such additional agents can also be present in the liposomes, can be present in different liposomes, or can be co-administered via a different route.

BRIEF DESCRIPTION OF THE DRAWINGS

FIG. 1a is a bar graph showing the effects of IB on cell growth in vitro, in terms of normalized cell viability. The bars shown are (from left to right) the cytotoxicity to RT2 cells (µg/ml), the proliferation of RT2 cells (µg/ml), and astrocytes (5 (µg/ml). The data show that IB was anti-invasive at concentrations at which it was not particularly cytotoxic or anti-proliferative.

FIG. 1b is a bar graph showing the dose dependent effects of IB on invasion using a Boyden Chamber Assay. The chart shows percent invasion relative to control, with the bars representing control, and IB dosed at 0.01 µg/ml, 0.1 µg/ml, 1 µg/ml, and 5 µg/ml. At concentrations above 20 µg/ml, IB was cytotoxic to cancer, and not just anti-invasive.

DETAILED DESCRIPTION

Figure 2:
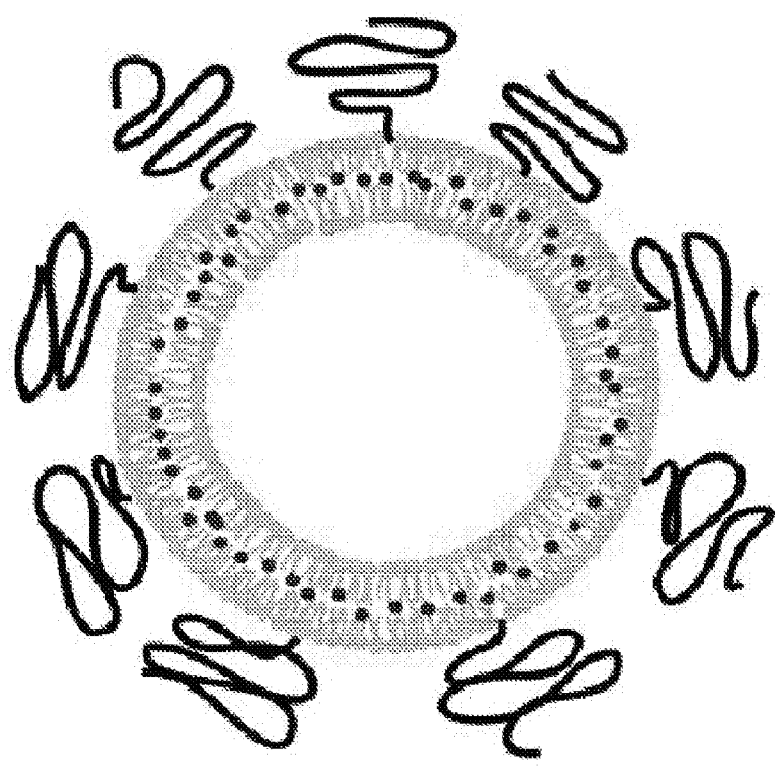
FIG. 2 is an illustration of a liposome including imipramine blue (also referred to herein as IB). The black dots within the walls of the liposome represent imipramine blue, and the "tails" on the outside of the liposome represent polyethylene glycol chains, which provide the liposome with "stealth" properties, such as an increased in vivo circulating half-life relative to liposomes that do not include polyethylene glycol chains.

The liposomal formulations and their use in treating invasive cancers, such as gliomas, will be better understood with reference to the following detailed description.

Imipramine Blue

The anti-cancer properties of imipramine blue are disclosed in PCT/US08/88495. The activity of imipramine blue against cancer cells is believed to be due to its ability to inhibit various Nox enzymes, and/or inhibit the production of reactive oxygen species (ROS). The ability of imipramine blue to inhibit the invasiveness of particularly aggressive and invasive tumors, such as gliomas, such as glioblastoma multiforme (also known as GBM, or malignant glioma) has not previously been reported. Imipramine blue is also able to inhibit the invasiveness of these tumors at concentrations below which it is cytotoxic.

Imipramine Blue has the formula:

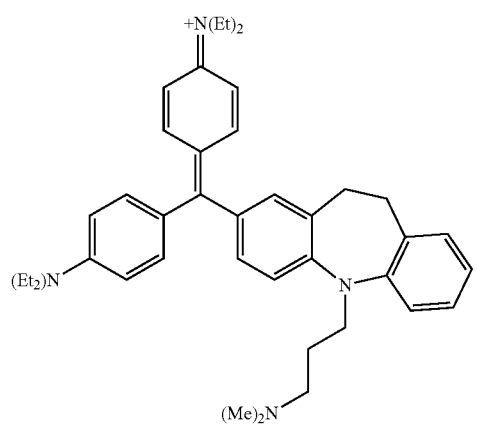

A resonance form of this structure is shown below:

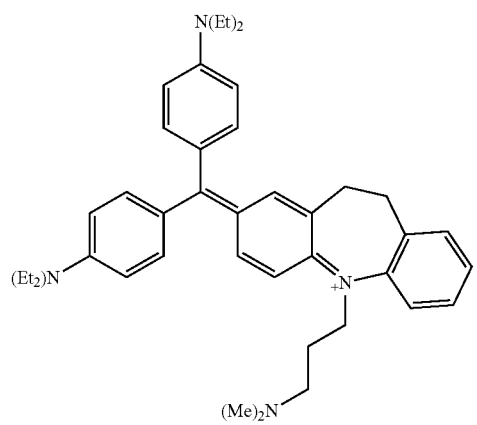

The compound is present in a salt form (e.g., as pharmaceutically acceptable salts). Examples of suitable pharmaceutically acceptable salts include inorganic acid addition salts such as sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with an acidic amino acid such as aspartate and glutamate; alkali metal salts such as sodium and potassium; alkaline earth metal salts such as magnesium and calcium; ammonium salt; organic basic salts such as trimethylamine, triethylamine, pyridine, picoline, dicyclohexylamine, and N,N'-dibenzylethylenediamine; and salts with a basic amino acid such as lysine and arginine. The salts can be in some cases hydrates or ethanol solvates. The stoichiometry of the salt will vary with the nature of the components.

Prodrug forms of imipramine blue can also be used. One such prodrug forms is that in which the iminium group is reduced, for example, with sodium cyanoborohydride. This prodrug can readily be reoxidized into the parent compound, and may offer various advantages over imipramine blue. That is, the prodrug form is less colored and more lipophilic (because the iminium salt is reduced to an amine). The compound can be more easily taken up by cells than imipramine blue, and may be less irritating in vivo. In tumors/blood vessels with high levels of superoxide/hydrogen peroxide, the prodrug can be readily oxidized to imipramine blue within the cell.

One or more of the amine groups can be converted to amide groups, which, upon hydrolysis, yield the amines, which can be oxidized to form the active compounds. Where the amide group is a trichloroacetyl amide group, the hydrolysis also produces the trichloroacetate salt, which can fight cancer via a different route than the active compounds (thus forming an in-situ drug cocktail from a single prodrug. Conditions for forming amides from amines and acids, or acid halides/anhydrides, are well known to those of skill in the art and need not be repeated here.

Synthesis of Imipramine Blue

Imipramine blue can be synthesized by reacting imipramine with Mischler's Ketone and an acid like phosphorus oxychloride ($POCl_3$), as shown below:

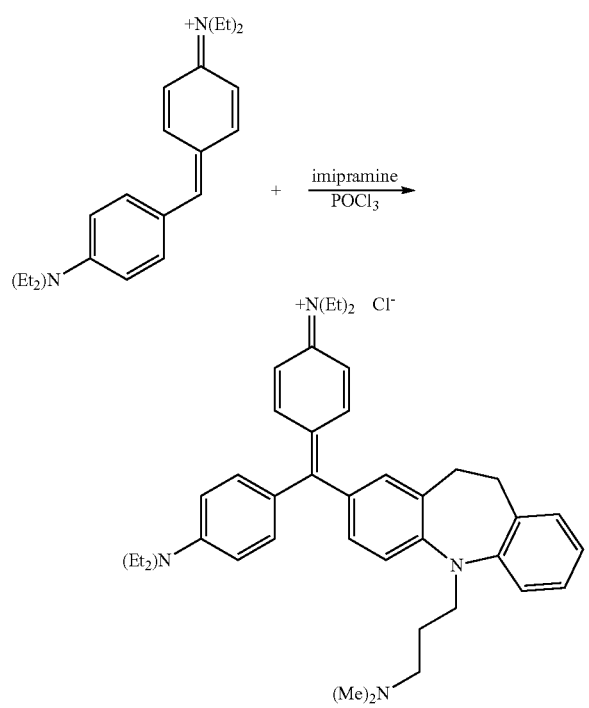

Liposome Components

There is a relatively high liver clearance of liposomes, which is not surprising, as this organ is one of the major sites of blood borne particulate removal. Accordingly, it can be advantageous to include one or more pegylated phospholipids in the liposomes.

It can also be advantageous that the liposomes have a melting point above body temperature (i.e., above 37° C.). For this reason, it can be advantageous to use pure phospholipids, preferably ones that are saturated, and have a carbon chain length of at least 16 carbons, preferably between 16 and 18 carbons. Distearoylphosphatidyl choline (DSPC) is a preferred phospholipid.

Cholesterol helps to stabilize the liposomes, and is preferably added in a sufficient amount to provide liposome stability.

Preparation of Liposomes

The liposomes which are used in the invention are small unilamellar liposomes of a size of less than 200 nm, preferably having a diameter of from about 50 to about 160 nm. As noted above, the vesicles are preferably comprised of chemically pure synthetic phospholipids having saturated aliphatic side chains and most preferably are prepared from phospholipids such as distearoyl phosphatidylcholine. Cholesterol is advantageously incorporated into the liposomes to increase the stability of the vesicles which are used in the disclosed process.

The liposomes preferably include imipramine blue, or a pharmaceutically acceptable salt thereof, but can optionally or additionally include other triaryl methane anti-tumor agents, such as those described in PCT/US08/88495, the contents of which are hereby incorporated by reference.

The liposomes can be prepared by dissolving the phospholipid and cholesterol in an appropriate organic solvent, such as chloroform, and evaporating the solvent to form a lipid film. If an ionophore is employed to load the imipramine blue, and/or a further diagnostic or therapeutic agent, into the liposomes, this compound may be added to the lipid solution before evaporation.

The dried lipid film is then rehydrated in an appropriate aqueous phase, such as phosphate-buffered saline or other physiologically appropriate solution. Water-soluble drugs or therapeutic agents may be contained in the hydrating solution, although if remote loading is desired a loading agent such as a chelating agent described above may be added to the hydrating solution to be encapsulated within the inner aqueous space of the liposome.

Upon the addition of the hydrating solution, liposomes of varying size spontaneously form and encapsulate a portion of the aqueous phase. Thereafter, the liposomes and suspending aqueous solution are subjected to a shear force such as extrusion, sonication, or processing through a homogenizer according to the method described in U.S. Pat. No. 4,753,788; to produce vesicles within the specified size.

The liposomes can then be processed to remove undesirable compounds from the suspending solution, for example the chelating agent or unencapsulated drug, which may be accomplished through processes such as gel chromatography or ultrafiltration.

If necessary, the product is then concentrated to remove excess buffer solution. Since the liposomes are smaller in size than 0.2 micron, they can be passed through a sterile 0.22 micron filter to remove any microorganisms which may be present in the suspension. Thereafter, the liposomes can be filled into sterilized glass containers and stoppered with a sterilized elastomer closure.

The liposomal compositions are ideally administered via intravenous injection, though can optionally be administered intracerebroventricularly. Suitable carriers for injection are well known to those of skill in the art, and include 5% dextrose solutions, saline, and phosphate buffered saline.

Ideally, before injection, the liposomal suspension is tested to confirm that the liposomes have not aggregated, as liposomal aggregation can be problematic.

In one embodiment, the liposomes are stored as a dry powder before use, for example, by freeze-drying a liposome suspension, and reconstituted immediately before use. Reconstitution of dried liposomes, and additional components used to stabilize liposomes during the drying process, are well known to those of skill in the art.

Combination Therapy

The combination therapy may be administered as (a) a single pharmaceutical composition which comprises imipramine blue and at least one additional pharmaceutical agent described herein, and a pharmaceutically acceptable excipient, diluent, or carrier; or (b) two separate pharmaceutical compositions comprising (i) a first composition comprising imipramine blue and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions can be administered simultaneously or sequentially and in any order.

In use in treating or preventing cancer, the imipramine blue described herein can be administered together with at least one other chemotherapeutic agent as part of a unitary pharmaceutical composition. Alternatively, the imipramine blue can be administered apart from the other anticancer chemotherapeutic agent. In this embodiment, the imipramine blue and the at least one other anticancer chemotherapeutic agent are administered substantially simultaneously, i.e. the compounds are administered at the same time or one after the other, so long as the compounds reach therapeutic levels for a period of time in the blood.

Combination therapy involves administering imipramine blue, or a pharmaceutically acceptable salt or prodrug thereof, in combination with at least one anti-cancer chemotherapeutic agent, ideally one which functions by a different mechanism (i.e., VEGF inhibitors, alkylating agents, and the like).

Examples of known anticancer agents which can be used for combination therapy include, but are not limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; and antibodies, such as Herceptin® and Rituxan®. Other known anti-cancer agents, which can be used for combination therapy, include arsenic trioxide, gamcitabine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine. Other classes of anticancer compounds that can be used in combination with the triphenyl methane analogues are described below.

Imipramine blue can be combined with alpha-1-adrenoceptor antagonists, such as doxazosin, terazosin, and tamsulosin, which can inhibit the growth of prostate cancer cell via induction of apoptosis (Kyprianou, N., et al., Cancer Res 60:4550-4555, (2000)).

Sigma-2 receptors are expressed in high densities in a variety of tumor cell types (Vilner, B. J., et al., Cancer Res. 55: 408-413 (1995)) and sigma-2 receptor agonists, such as CB-64D, CB-184 and haloperidol, activate a novel apoptotic pathway and potentiate antineoplastic drugs in breast tumor cell lines (Kyprianou, N., et al., Cancer Res. 62:313-322 (2002)). Accordingly, the triphenyl methane analogues can be combined with at least one known sigma-2 receptor agonists, or a pharmaceutically acceptable salt of said agent.

Imipramine blue can be combined with lovastatin, a HMG-CoA reductase inhibitor, and butyrate, an inducer of apoptosis in the Lewis lung carcinoma model in mice, can potentiate antitumor effects (Giermasz, A., et al., Int. J. Cancer 97:746-750 (2002)). Examples of known HMG-CoA reductase inhibitors, which can be used for combination therapy include, but are not limited to, lovastatin, simvastatin, pravastatin, fluvastatin, atorvastatin and cerivastatin, and pharmaceutically acceptable salts thereof.

Certain HIV protease inhibitors, such as indinavir or saquinavir, have potent anti-angiogenic activities and promote regression of Kaposi sarcoma (Sgadari, C., et al., Nat. Med. 8:225-232 (2002)). Accordingly (in addition to forming triphenyl methane analogues of these compounds), the triphenyl methane analogues can be combined with HIV protease inhibitors, or a pharmaceutically acceptable salt of said agent. Representative HIV protease inhibitors include, but are not limited to, amprenavir, abacavir, CGP-73547, CGP-61755, DMP-450, indinavir, nelfinavir, tipranavir, ritonavir, saquinavir, ABT-378, AG 1776, and BMS-232,632.

Synthetic retinoids, such as fenretinide (N-(4-hydroxyphenyl)retinamide, 4HPR), can have good activity in combination with other chemotherapeutic agents, such as cisplatin, etoposide or paclitaxel in small-cell lung cancer cell lines (Kalemkerian, G. P., et al., Cancer Chemother. Pharmacol. 43:145-150 (1999)). 4HPR also was reported to have good activity in combination with gamma-radiation on bladder cancer cell lines (Zou, C., et al., Int. J. Oncol. 13:1037-1041 (1998)). Representative retinoids and synthetic retinoids include, but are not limited to, bexarotene, tretinoin, 13-cis-retinoic acid, 9-cis-retinoic acid, .alpha.-difluoromethylornithine, ILX23-7553, fenretinide, and N-4-carboxyphenyl retinamide.

Proteasome inhibitors, such as lactacystin, exert anti-tumor activity in vivo and in tumor cells in vitro, including those resistant to conventional chemotherapeutic agents. By inhibiting NF-kappaB transcriptional activity, proteasome inhibitors may also prevent angiogenesis and metastasis in vivo and further increase the sensitivity of cancer cells to apoptosis (Almond, J. B., et al., Leukemia 16:433-443 (2002)). Representative proteasome inhibitors include, but are not limited to, lactacystin, MG-132, and PS-341.

Tyrosine kinase inhibitors, such as STI571 (Imatinib mesilate, Gleevec®), have potent synergetic effects in combination with other anti-leukemic agents, such as etoposide (Liu, W. M., et al. Br. J. Cancer 86:1472-1478 (2002)). Representative tyrosine kinase inhibitors include, but are not limited to, Gleevec®, ZD1839 (Iressa®), SH268, genistein, CEP2563, SU6668, SU11248, and EMD121974.

Prenyl-protein transferase inhibitors, such as farnesyl protein transferase inhibitor R115777, possess antitumor activity against human breast cancer (Kelland, L. R., et. al., Clin. Cancer Res. 7:3544-3550 (2001)). Synergy of the protein farnesyltransferase inhibitor SCH66336 and cisplatin in human cancer cell lines also has been reported (Adjei, A. A., et al., Clin. Cancer. Res. 7:1438-1445 (2001)). Prenyl-protein transferase inhibitors, including farnesyl protein transferase inhibitor, inhibitors of geranylgeranyl-protein transferase type I (GGPTase-I) and geranylgeranyl-protein transferase type-II, or a pharmaceutically acceptable salt of said agent, can be used in combination with the triphenyl methane analogues described herein. Examples of known prenylprotein transferase inhibitors include, but are not limited to, R115777, SCH66336, L-778,123, BAL9611 and TAN-1813.

Cyclin-dependent kinase (CDK) inhibitors, such as flavopiridol, have potent, often synergetic, effects in combination with other anticancer agents, such as CPT-11, a DNA topoisomerase I inhibitor in human colon cancer cells (Motwani, M., et al., Clin. Cancer Res. 7:4209-4219, (2001)). Representative cyclin-dependent kinase inhibitors include, but are not limited to, flavopiridol, UCN-01, roscovitine and olomoucine.

Certain COX-2 inhibitors are known to block angiogenesis, suppress solid tumor metastases, and slow the growth of implanted gastrointestinal cancer cells (Blanke, C. D., Oncology (Hunting) 16 (No. 4 Suppl. 3):17-21 (2002)). Representative COX-2 inhibitors include, but are not limited to, celecoxib, valecoxib, and rofecoxib.

IKB-α phosphorylation inhibitors, such as BAY-11-7082 (an irreversible inhibitor of IKB-α phosphorylation) are also known to induce apoptosis, or to enhance the effectiveness of other agents at inducing apoptosis. These inhibitors can also be used in combination with the compounds described herein.

Any of the above-mentioned compounds can be used in combination therapy with the imipramine blue.

The imipramine blue can also be used in conjunction with surgical tumor removal, by administering the compounds before and/or after surgery, and in conjunction with radiation therapy, by administering the compounds before, during, and/or after radiation therapy.

The appropriate dose of the imipramine blue and, optionally, additional agents is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder.

When treating cancers, an effective amount of the imipramine blue is an amount sufficient to suppress the growth of the tumor(s), and, ideally, is a sufficient amount to shrink the tumor, and, more ideally, to destroy the tumor, inhibit its invasiveness, and/or inhibit its metastasis. Cancer can be prevented, either initially, or from re-occurring, by administering the compounds described herein in a prophylactic manner. Preferably, the effective amount is sufficient to obtain the desired result, but insufficient to cause appreciable side effects.

The effective dose can vary, depending upon factors such as the condition of the patient, the severity of the cancer, and the manner in which the pharmaceutical composition is administered. The effective dose of compounds will of course differ from patient to patient, but in general includes amounts starting where desired therapeutic effects occur but below the amount where significant side effects are observed.

The compounds, when employed in effective amounts in accordance with the method described herein, are selective to certain cancer cells, but do not significantly affect normal cells.

For human patients, the effective dose of typical compounds generally requires administering the compound in an amount of at least about 1, often at least about 10, and frequently at least about 25 μg/24 hr/patient. The effective dose generally does not exceed about 500, often does not exceed about 400, and frequently does not exceed about 300 μg/24 hr/patient. In addition, administration of the effective dose is such that the concentration of the compound within the plasma of the patient normally does not exceed 500 ng/mL and frequently does not exceed 100 ng/mL.

Diagnostic Agents

A wide variety of diagnostic agents may be incorporated in the inner aqueous space or the lipid bilayer of the liposomes by methods which will be apparent to one of skill in the art. In the following examples a chelating compound and an ionophore are employed for loading external cations for radiolabelling into the vesicles. The preferred ionophore is A23187, but other useful ionophores are polyethers such as lasalocid A(X-537A) and 5-bromo derivatives of lasalocid; cyclic depsipeptides such as beauvericin; and cyclic peptides such as valinomylin. The chelating agent is preferably nitriloacetic acid (NTA) although other chelators may also be used.

Methods of Using the Compounds and/or Pharmaceutical Compositions

The pharmaceutical compositions described herein can be used to treat cancers, preferably, but not limited to, invasive cancers such as gliomas.

The cancers include, but are not limited to, those in which one of the Nox enzymes is present in elevated concentrations (i.e., Nox 1, Nox 4, and the like), or those in which cancer growth is mediated by reactive oxygen species (ROS).

Representative disorders that can be treated include neoplasms, such as hemangiomas, and malignant tumors, for example, those which arise in the setting of autocrine loops involving vascular endothelial growth factor (VEGF) and its major mitogenic receptor vascular endothelial growth factor receptor 2. Representative malignant tumors include malignant endothelial tumors such as melanoma.

Representative malignant tumors include malignant endothelial tumors such as melanoma. Additional cancers that can be treated include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., plasma cell leukemia, acute lymphocytic leukemia, acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), including NF-KB mutant and Velcade Resistant lymphoma cells, multiple myeloma, PI3 kinase deficient myeloma, Waldenstrom's macroglobulinemia, and heavy chain disease, and malignant forms of these cancers. Additionally, the compounds can be used in assays involving lymphoblastoid and EBV positive cells.

In one embodiment, the cancer is melanoma, rectal carcinoma, colon carcinoma, breast carcinoma, ovarian carcinoma, small cell lung carcinoma, colon carcinoma, chronic lymphocytic carcinoma, hairy cell leukemia, esophogeal carcinoma, prostate carcinoma, breast cancer, myeloma, or lymphoma. It is believed that these cancers have circulating levels of tNOX (which may include Nox4 or other Nox enzymes) present in the sera of patients suffering from the cancer (see, for example, U.S. Pat. No. 5,605,810, which is hereby incorporated by reference in its entirety).

In some embodiments, the patient already has cancer and is undergoing treatment for the cancer, and may or may not have tumor metastasis (i.e., secondary cancer).

In other embodiments, the compositions are active at inhibiting hypoxia-inducible factor HIF2a expression, and this activity aids in the treatment of tumors resistant to standard chemoradiotherapy. Hypoxia-inducible factor HIF2alpha (HIFalphas) regulates the expression of a variety of genes encoding proteins related to angiogenesis and to anaerobic metabolism of cells exposed to hypoxic stress (Koukourakis et al., Int J Radiat Oncol Biol Phys. 2002 Aug. 1;53(5):1192-202.) HIF2a overexpression is significantly associated with high microvessel density (p=0.02, respectively) and with VEGF expression (p=0.005), and VEGF/KDR-activated tumor vasculature is more frequent in HIF2a-overexpressing tumors (p=0.02). High HIF2a levels have been associated with incomplete response to chemoradiation (p=0.02, respectively), and overexpression of HIF2a is related to locally aggressive behavior, intensification of angiogenesis, and resistance to carboplatin chemoradiotherapy.

As discussed in PCT/US08/88495, imipramine blue was evaluated in a HIF2a expression model, and was shown to inhibit around 90% of the HIF2a expression. In this expression model, WM35 PKB cells are exposed to 5 micromolar of test compounds for 24 hours. At the end of this period, cells are harvested for RNA, which is then reverse transcribed into cDNA, and levels of HIF2a message are quantified using quantitative RT-PCR and corrected for a housekeeping RNA message. As demonstrated using this assay, these compounds can act as direct NADPH oxidase inhibitors, as well as superoxide scavengers that absorb superoxide produced by defective mitochondria or other cellular processes.

The cancer may be manifested in the form of a tumor, such as a tumor of epithelial tissue, lymphoid tissue, connective tissue, bone, or central nervous system.

The compositions can also be used as adjunct therapy in combination with existing therapies in the management of the aforementioned types of cancers. In such situations, it is preferably to administer the active ingredients to in a manner that optimizes effects upon cancer cells, including drug resistant cancer cells, while minimizing effects upon normal cell types. While this is primarily accomplished by virtue of the behavior of the compounds themselves, this can also be accomplished by targeted drug delivery and/or by adjusting the dosage such that a desired effect is obtained without meeting the threshold dosage required to achieve significant side effects.

The present invention will be better understood with reference to the following non-limiting examples.

EXAMPLE 1

In Vitro Compound Screen

An aggressive rat astrocytoma cell line, RT2, was maintained in vitro. This cell line was used to test 24 compounds at varying concentrations in cytotoxicity and proliferation assays using CCK8 (Dojindo), a tetrazolium salt based assay. Compounds without detrimental effects on viability and growth were tested using the Boyden chamber invasion assay at 48 hours. Compounds were also tested for viability against astrocyte cultures using CCK8. Of these compounds, several were identified as anti-invasive. However, several compounds were toxic to astrocytes in culture and several were cytotoxic and not in fact anti-invasive. Several of these compounds are, like IB, triaryl methanes disclosed in PCT/US08/88495, and IB showed the highest anti-invasive properties of the triaryl methanes tested.

Figure 3A:
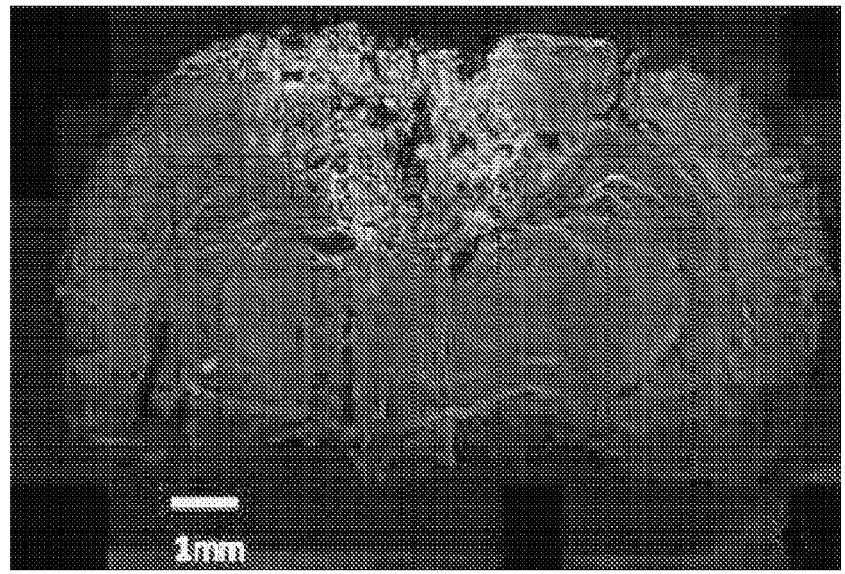
FIGS. 3a and 3b are photographs showing the tumor progression at Day 11 in Fischer 344 Rats using DAPI stain for cell nuclei.
Figure 3B:
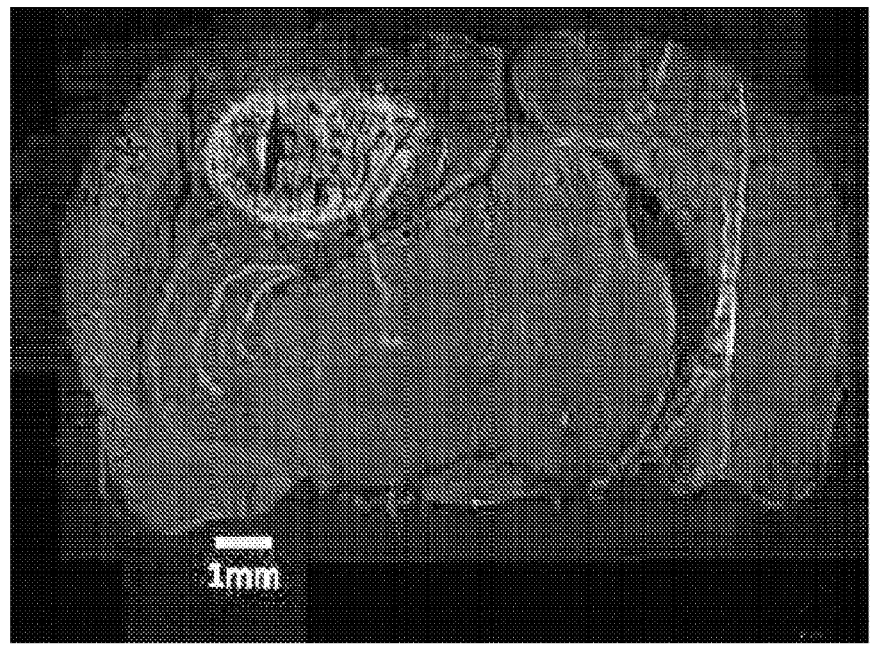

One compound, IB was determined to be anti-invasive while not cytotoxic and not antiproliferative. It also is benign to astrocyte co-culture making it safer for delivery to the brain (FIG. 3a). The compound is blue in color with an absorbance at 610 nm making it easily assayable. This compound offers dose-dependent anti-invasive response against malignant glioma cell line RT2A in culture (FIG. 3b). At concentrations above 20 μg/ml, IB was cytotoxic to cancer and not just anti-invasive.

Some of the compounds are proprietary compounds, so their identity is not provided herein. However, a listing of the non-proprietary compounds is provided below. Where the structure is well known, it is not provided, and where the structure is not well known, it is provided at the end of the list.

1. Honokiol
2. Honokiol Diketone Fulvene
3. Magnolol
4. Protected Magnolol (i.e., wherein the hydroxy groups are protected with protecting groups)
5. GdCu$_3$
6. Honokiol Diepoxides (i.e., wherein the double bonds in honokiol are replaced with epoxide groups)
7. Thiobendazole Blue—the product of the reaction of thiobendazole and Mischler's ketone under reactions conditions described in PCT/US08/88495
8. Carbazole Blue
9. Imipramine Blue
10. Honokiol in which one or both hydroxy groups have been replaced by dichloroacetate and trichloroacetate esters
11. DDT Black
12. Tetrafluoro Brilliant Green
13. The triaryl methane resulting from the reaction of Mischler's ketone and Promethazine under conditions described in in PCT/US08/88495
14. Saccharine Blue (structures shown below)
15. Thymol Green—the triaryl methane resulting from the reaction of Mischler's ketone and thymol under conditions described in in PCT/US08/88495, believed to have the structure shown below.
16. Geldanamycin

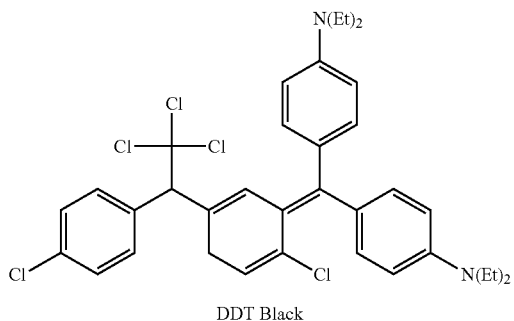

DDT Black

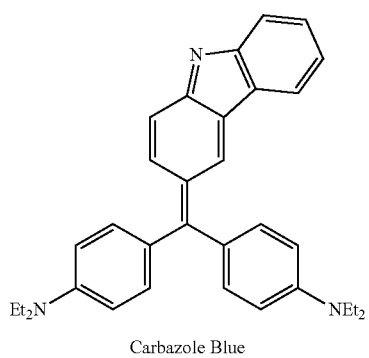

Carbazole Blue

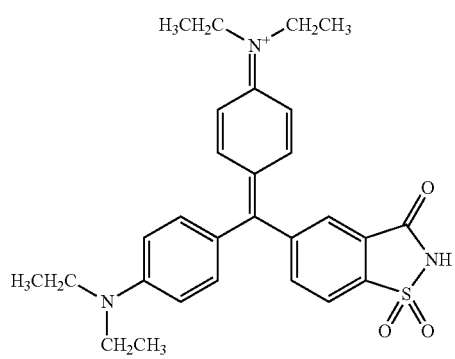

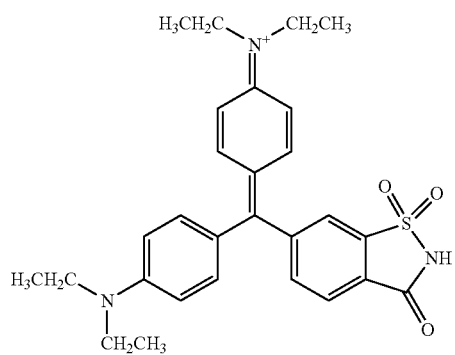

Saccharine blue—the reaction product of saccharine with Mischler's Ketone includes one or both of these compounds

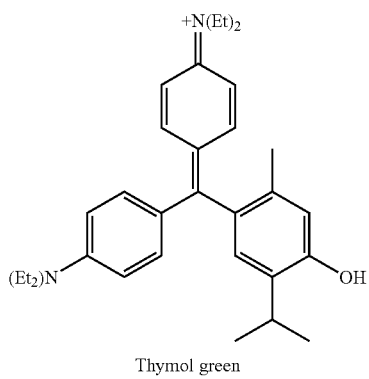

Thymol green

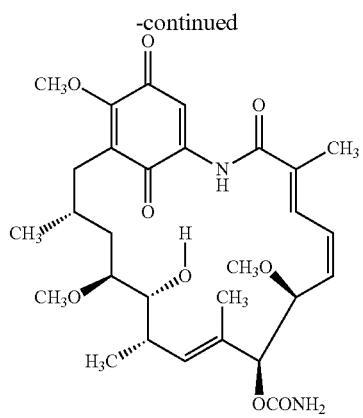

Geldanamycin

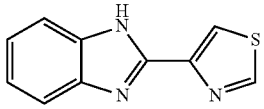

Thiobendazole (thiobendazole blue is obtained by reacting this compound and Mischler's ketone under conditions as described in PCT/US08/88495).

EXAMPLE 2

Preparation and Evaluation of Liposomes Containing Imipramine Blue

This example evaluated the effectiveness of IB-containing liposomes in a live rat model.

Nanocarrier Synthesis:

Liposomes were made from DSPC (85 mol %), DSPE-PEG (5 mol %, Avanti Polar Lipids)), and cholesterol (10 mol %, Sigma) by dissolving the lipids and 2 mg/ml of IB in ethanol. The solution was hydrated using phosphate buffered saline at 70° C. to yield liposomes. Liposomes were extruded to a size of 160 nm as assessed by dynamic light scattering. Unbound drug was removed via sepharose column separation and then diafiltrated to a final IB concentration of 3.5 mg/ml.

In Vivo Animal Studies:

For tumor inoculation, 8-10 week old week old Fischer 344 rats were anesthetized using 2-3% Isoflurane inhalant. A 1 cm incision to the skull was made and a 2 mm burr hole was drilled 2 mm lateral and 6 mm posterior to bregma. 250,000 cells were injected in 10 μl of Leibovitz media over a period of 10 minutes using a Hamilton syringe. The hole was filled with bone wax and the wound closed.

On days 4 and 7 of tumor growth, 16 mg/kg (IB concentration) of IB-liposomes were injected via the tail vein. On Day 11 following tumor inoculation animals were sacrificed by intracardial perfusion. Brains were removed, photographed, fixed, embedded in OCT and sectioned. Slides were collected, stained using DAPI and imaged. Image analysis was conducted in a blinded fashion to quantify invasiveness.

The results are shown in FIGS. 3a and 3b, which show tumor progression at Day 11 in Fischer 344 rats using DAPI stain for cell nuclei. As shown in FIG. 3a, untreated tumor shows chaotic borders nad infiltrative tumor cells, whereas FIG. 3b shows that IB-liposome treated tumors show a more encapsulated morphology with well-defined borders between the tumor and the healthy brain.

Results:

We have identified imipramine blue as a potent anti-invasive agent for glioma, and have efficiently encapsulated IB in liposomal nanocarriers. In preliminary studies, IB-liposomes significantly impacted glioma invasion in vivo.

Conclusions:

In this study, we have shown use of a novel anti-invasive compound, imipramine blue, to inhibit invasion in vitro and in vivo when delivered in nanocarriers. Therefore, anti-invasive compounds may be used for treatment of invasive tumors in conjunction with cytotoxic therapy or surgery. The imipramine blue can be co-encapsulated and delivered with common chemotherapeutics and used in conjunction with tumor resection.

EXAMPLE 3

Further Evaluation of IB-Containing Liposomes

This example evaluated the effectiveness of IB-containing liposomes in a live rat model, at a slightly higher dosage of IB within the liposomes than was present in Example 2.

Nanocarrier Synthesis:

Liposomes were made from DSPC (85 mol %), DSPE-PEG (5 mol %, Avanti Polar Lipids)), and cholesterol (10 mol %, Sigma) by dissolving the lipids and IB in ethanol. The solution was hydrated using phosphate buffered saline at 70° C. to yield liposomes. Liposomes were extruded to a size of 160 nm as assessed by dynamic light scattering. Unbound drug was removed via sepharose column separation and then diafiltrated to a final IB concentration of 7-8 mg/ml.

Pharmacokinetics and Biodistribution Studies:

Animals were injected via tail vein with 20 mg/kg liposomal or free IB. Orbital blood draws were performed at intervals and blood collected, centrifuged, and serum read at 610 nm absorbance for pharmacokinetics. For biodistribution, animals were perfused with saline, organs collected, homogenized, and drug extracted with DMSO and read at 610 nm absorbance for pharmacokinetics. For biodistribution, animals were perfused with saline, organs collected, homogenized, and drug extracted with DMSO and read at 610 nm absorbance.

Figure 4:
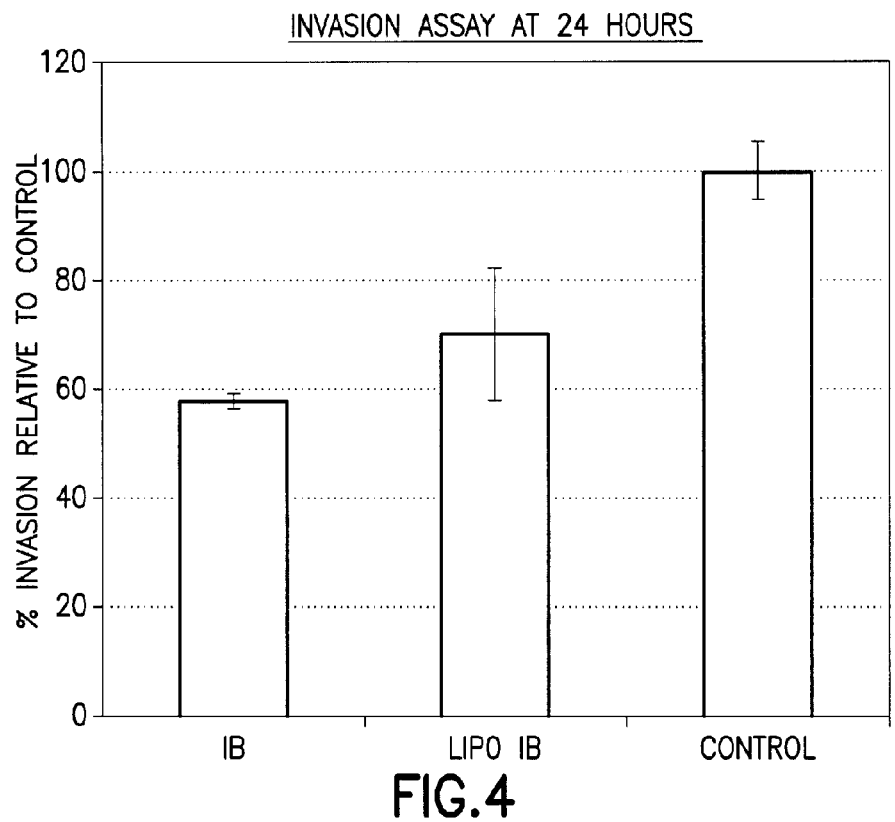
FIG. 4 is a chart showing the results of an invasion assay at 24 hours, showing invasion (%) over time (24 hours). The control shows 100 percent invasion, free imipramine blue ("IB") showed around 60% invasion, and liposomal IB ("lipo IB") showed around 70% invasion.

An invasion assay was performed at 24 hours. The encapsulated formulation was compared to tree drug in vitro and was still active as an anti-invasive agent. Encapsulation of the compound in liposomes is reproducible and consistent between batched. The data is shown in FIG. 4, where the control shows 100 percent invasion, the liposomal IB formulation showed around 70% invasion, and free IB showed around 60% invasion.

Figure 5:
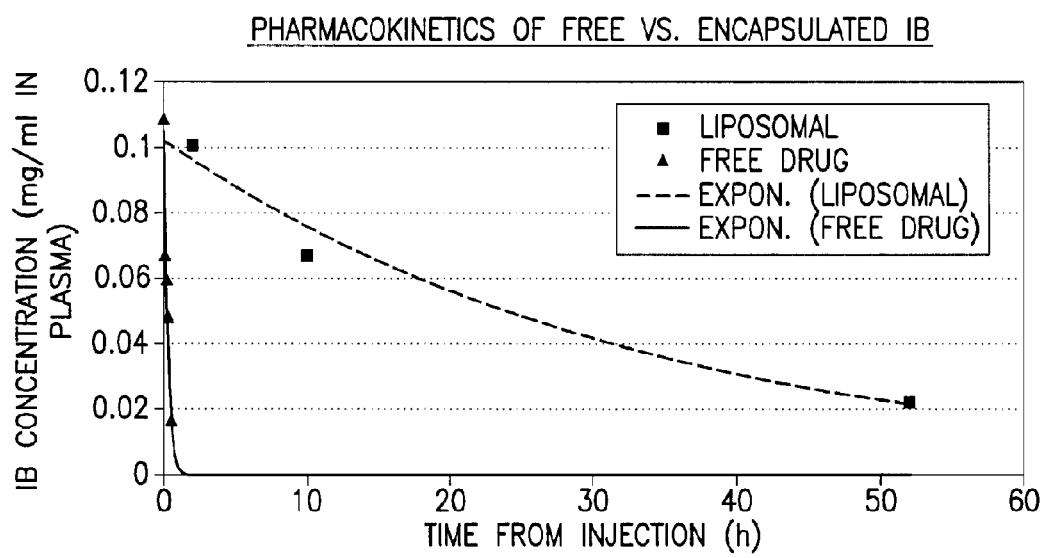
FIG. 5 is a chart showing the pharmacokinetics of free versus encapsulated imipramine blue, in terms of plasma concentration (mg/ml) over time (hours).

The circulation time of the free imipramine blue was tested in a Cremaphor formulation similar to that of paclitaxel. The final half-life was around 11 minutes due to its quick absorption into body tissues. The drug was encapsulated in liposomes, and hielded a half-life of 21 hours and accumulation in the tumor. The data is shown in FIG. 5.

In Vivo Treatment with Imipramine Blue:

All protocols were approved by the Georgia Institute of Technology Institutional Animal Use For tumor inoculation, 12 week old Fischer 344 rats were anesthetized using 2-3% Isoflurane inhalant. A 1 cm incision to the skull was made and a 2 mm burr hole was drilled 2 mm lateral and 6 mm posterior to bregma. 200,000 cells were injected in 10 µl of Leibovitz media over a period of 10 minutes using a Hamilton syringe. On two days after inoculation, IB-liposome was delivered in saline via the tail vein. On Day 11 following tumor inoculation, animals were sacrifieced by intracardial perfusion with saline and then 4% paraformaldehyde. Brains were removed, fixed, embedded and sectioned through the tumor. Slides were collected, stained using DAPI, and imaged using Neurolucida.

Figure 6A:
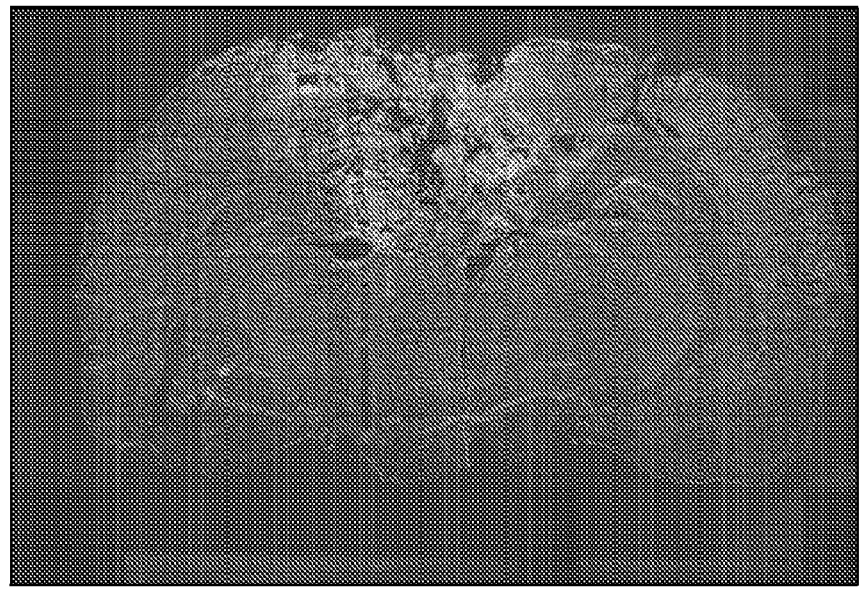
FIGS. 6A and 6B are photomicrographs showing untreated tumors, with green showing healthy tumor cells and blue indicating cell nuclei for unhealthy tumor cells and normal brain structures.
Figure 6B:
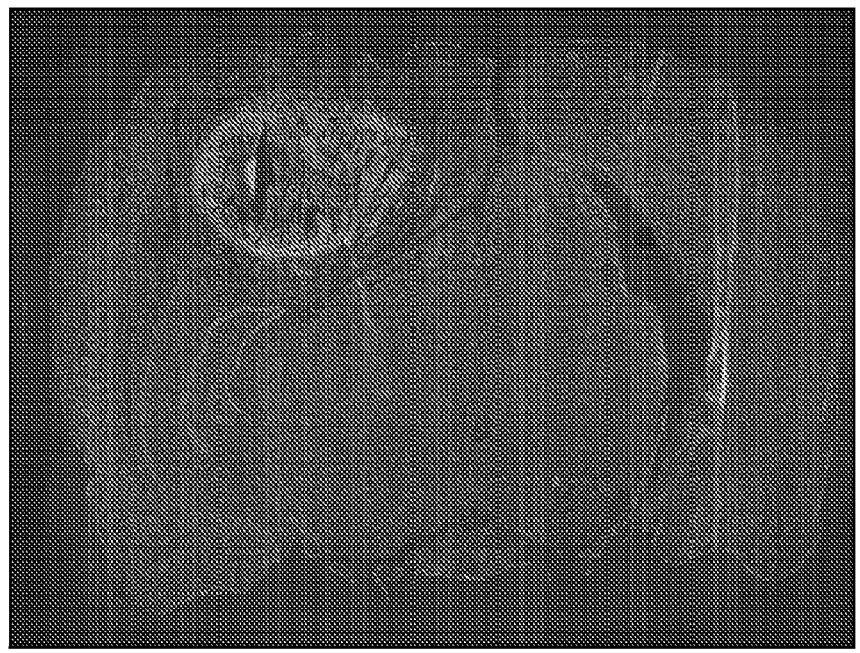

Animals were treated with encapsulated IB at two time points after tumor inoculation. The results of the treatment on day 11 revealed a change in the phenotype of the tumor between treated and untreated tumors in terms of invasion into surrounding brain tissue. FIG. 6a shows a photograph of an untreated tumor, with green being healthy tumor cells and blue indicating cell nuclei for unhealthy tumor cells and normal brain structures. FIG. 6b shows a photograph of a treated tumor (smaller in size than the untreated tumor), which was similarly stained, and which showed more unhealthy tumor cells and a more of a contained (i.e., less invasive) structure.

EXAMPLE 4

In Vivo and In Vitro Evaluation of Imipramine Blue ("IB") and Combination of IB and Doxorubicin ("DOX")

According to the National Cancer Institute, brain tumors are the leading cause of solid tumor cancer death in children. Glioblastoma Multiforme (GBM) is a highly infiltrative and lethal form of brain tumor. These tumors are characterized as being unresponsive to traditional cancer treatments, and result in poor prognosis and survival due to their invasive and diffusive nature.

Common treatments focus on reducing the bulk of the tumor via radiation, chemotherapy, and surgical resection, which leads to residual tumor at the site and recurrence. This example evaluated a new strategy for treatment, which focuses on inhibiting the invasion of these tumors, alone and in conjunction with common therapeutic strategies. While not wishing to be bound to a particular theory, it is believed that if the tumor can be effectively contained via treatment, then it should be more responsive to chemotherapeutics, resection, and radiation, and thus yield a better prognosis after treatment.

The compound imipramine blue ("IB") is a novel compound that inhibits invasion of glioblastoma in vitro and shows promise in vivo in a rat model of GBM. Using this compound as a chemopreventive agent to inhibit progression of lower grade gliomas to higher grade gliomas, as well as treatment of high grade gliomas, is a promising therapeutic alternative.

The use of an encapsulated anti-invasive agent alone, and in conjunction with common cancer therapy strategies, can yield a more promising prognosis in glioblastoma multiforme by affecting the phenotype of the tumor. The goal of this study was to determine the efficacy of the agent in vivo using a tumor targeted delivery system. To accomplish this goal, IB was synthesized and characterized in vitro. Nanocarriers that deliver IB were prepared and characterized in vitro and in vivo assays, and part of the characterization included pharmacokinetics and biodistribution. The efficacy of a particular type of IB nanocarrier, a liposome, was evaluated in vivo, including an assessment of its effects on survival and phenotype. Co-encapsulated chemotherapeutic/anti-invasive nanocarriers were prepared and characterized in vivo.

Imipramine Blue Shows Promising Anti-Invasive Qualities In Vitro.

Figure 7:
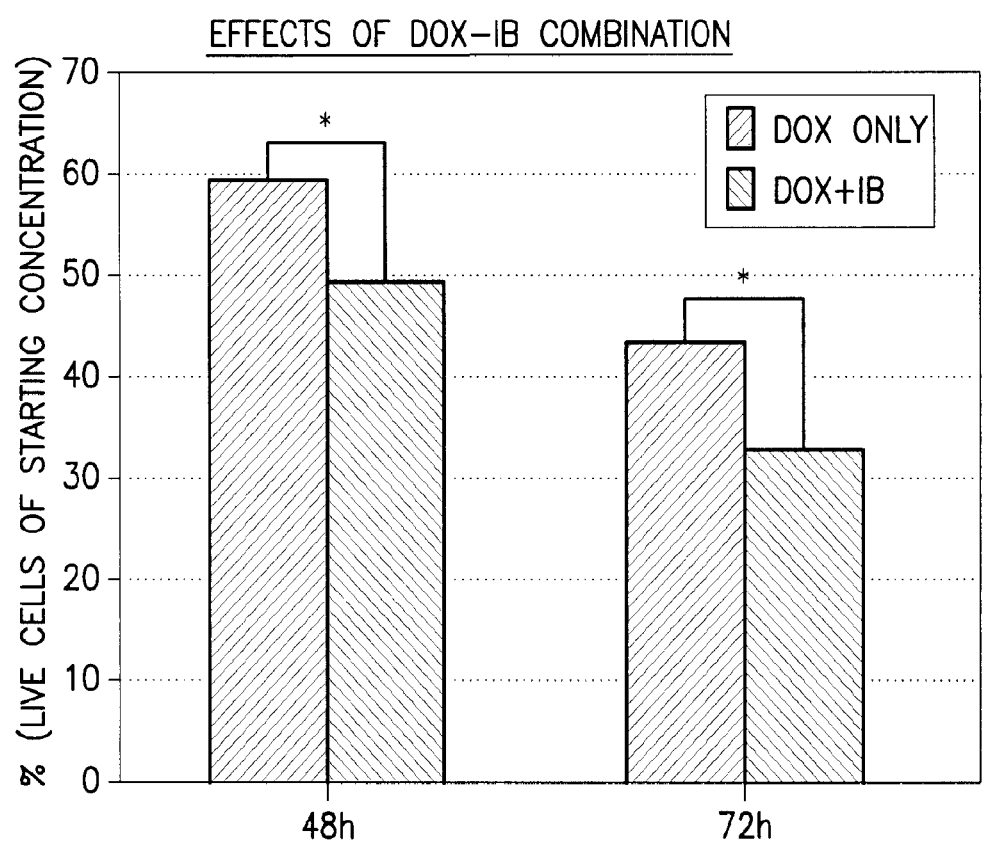
FIG. 7 is a chart showing the results of in vitro combination of Doxorubicin ("Dox") and imipramine blue ("IB") against RT2 glioma cells. Cells were quantified by metabolic assay (CCK-8, Dojindo) and compared to starting cell concentrations (%). Cells were treated for 2 hours with Dox or Dox+IB and media replaced. Cells were quantified at 48h (p=0.04) and 72h (p=0.05). Co-treatment increased cell death compared to Dox alone.
Figure 8:
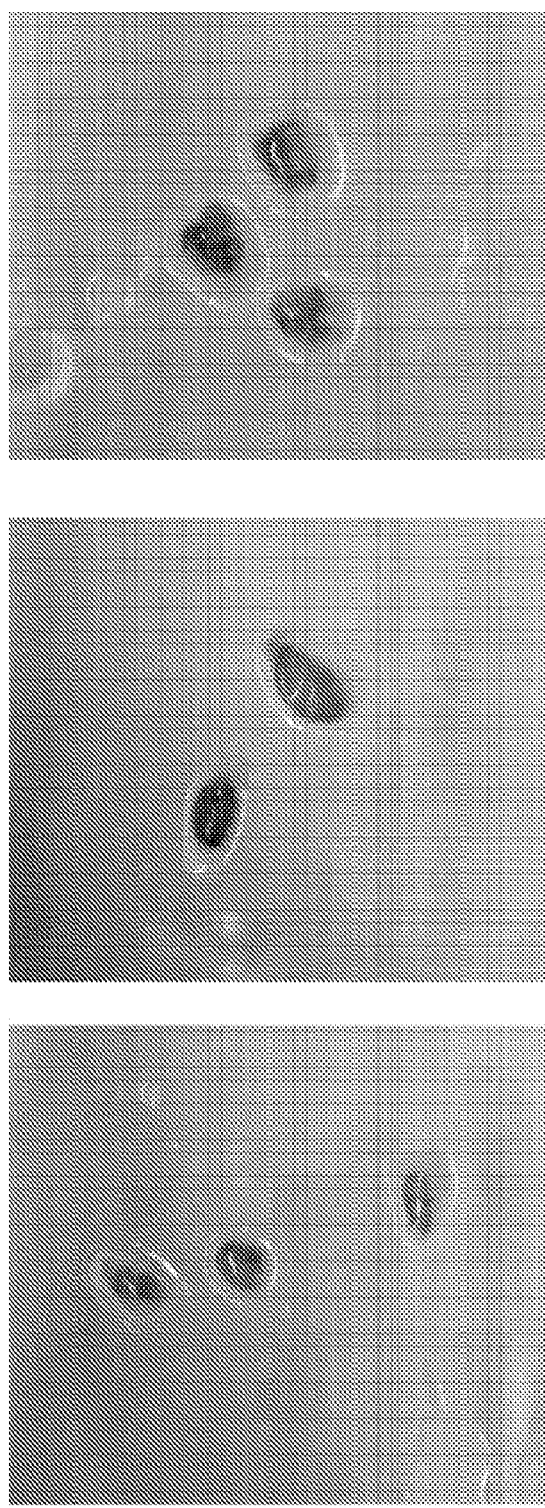
FIG. 8 is a series of three photographs of lymph nodes collected from rats given subcutaneous injections of liposomal IB. The nodes are tinted blue from the color of the drug, indicating that the drug was delivered.

Pharmacokinetic studies on the alteration in bioavailability of IB in vivo show an increase in half-life from 11 minutes to 21 hours when liposomally encapsulated. Preliminary survival studies indicate that the drug slightly prolongs survival of animals with the highly aggressive RT2 glioma model from the control time of 13.4 days to 14.9 days (n=6 per group, p=0.05). This increase in survival is minor, however, the change in phenotype of the tumor was promising. Further, in vitro studies looking at the effect of co-delivery of IB and Doxorubicin indicated a synergistic effect on cell death (FIG. 7). Also, the liposomal IB was delivered via subcutaneous administration in rats and effectively traveled to the lymph nodes, indicating the possibility for delivery to other metastatic cancers. These preliminary results are evidenced by the blue color of lymph nodes collected from animals treated with liposomal IB (FIG. 8).

Figure 9A:
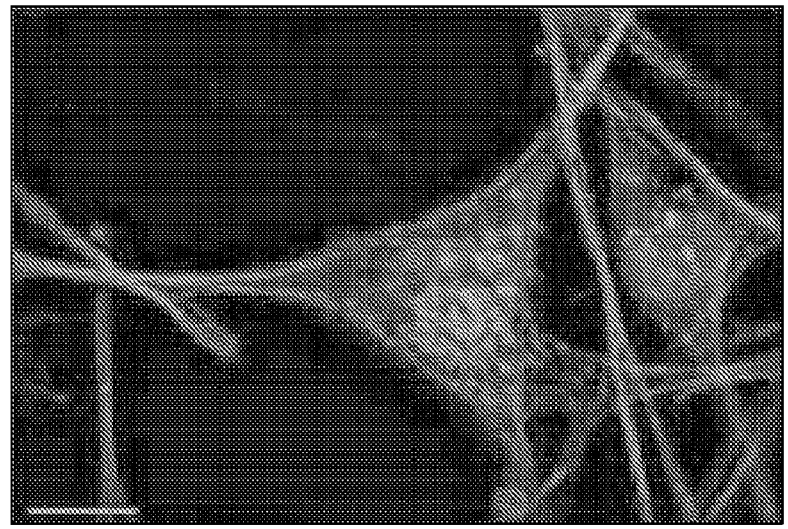
FIGS. 9A and 9B are photomicrographs showing the results of in vitro treatment of RT2 glioma cells with IB. Cells were treated with ethanol (6A) or IB (6B) and stained for actin (red) and nuclei (blue).
Figure 9B:
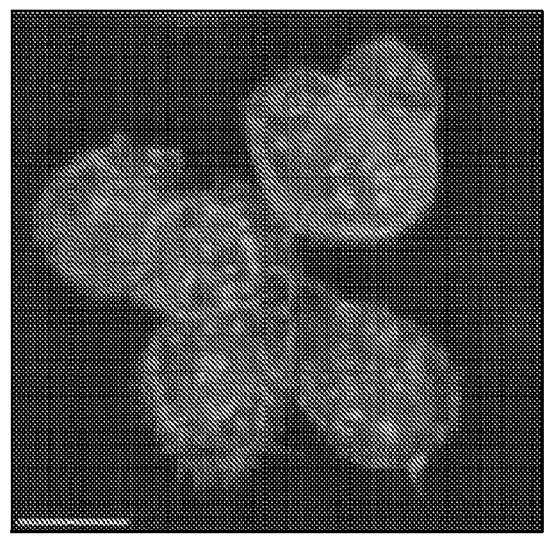

The ability of IB to impact invasion capability of glioma cells was tested further in vitro. Cells were treated for 24 hours with either IB dissolved in ethanol or an equivalent volume of ethanol. FIGS. 9A and 9B demonstrate how IB alters the arrangement of the cytoskeleton of glioma cells, which will ultimately impede the ability of these cells to invade surrounding healthy tissues.

Figure 10:
FIG. 10 is a photograph showing untreated (left) and nano-IB treated (right) axial brain sections stained with DAPI for nuclei showing tumor size/contra-lateral invasion difference after treatment.
Figure 11A:
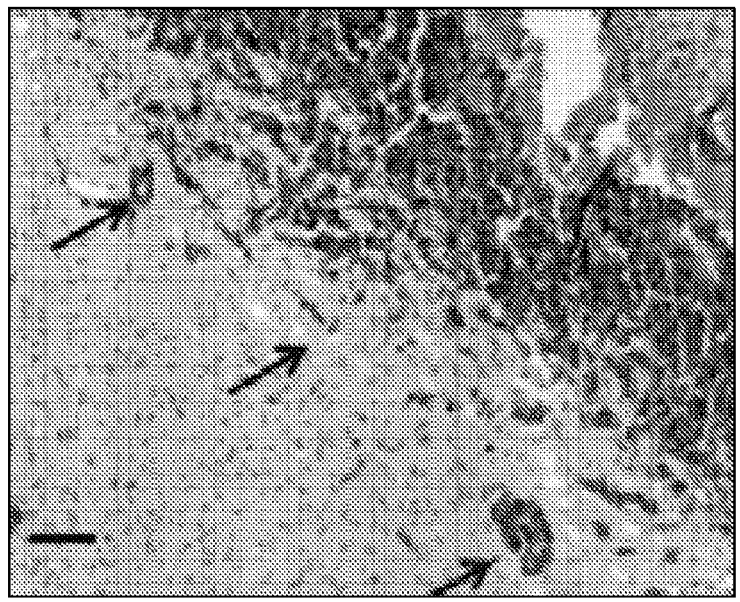
FIGS. 11A and 11B are H&E tumor border images of untreated (5A) and nano-IB treated (5B), showing the difference between invasion of tumor cells into healthy tissue.
Figure 11B:
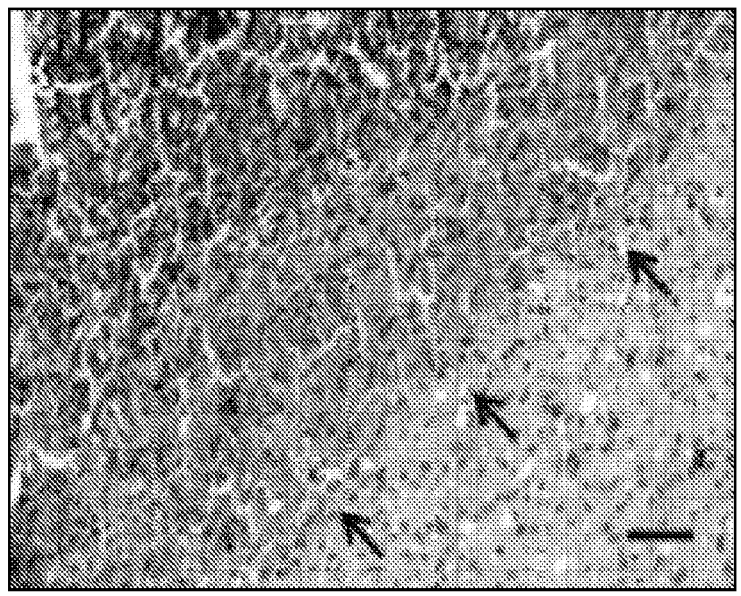

In vivo studies were conducted on a rat RT2 glioma model to determine the effect of nano-IB on tumor invasion into surrounding tissue. Adult male rats were inoculated with 200 k RT2 astrocytoma cells into the posterior cortex via syringe. At 4 and 7 days after inoculation, nano-IB was delivered i.v. On day 11 after tumor inoculation, brains were sectioned and counterstained with DAPI for tumor visualization. The treated tumors were smaller, denser, and exhibited less invasion than the untreated control tumors, indicating the anti-invasive effect of nano-IB (FIG. 10). The tumor boundaries of H&E stained sections were visualized, and the treate11A and 11B).

In preparation for in vivo studies evaluating the effect of IB in combination with chemotherapeutics (doxorubicin), nano-carrier formulations loaded with both IB and doxorubicin were prepared and optimized for in vivo delivery. Nano-IB was formulated in ammonium sulfate, which was used to facilitate the remote loading of doxorubicin. Unencapsulated drugs were removed through column chromatography, and the nanocarriers were concentrated through diafiltration. Co-encapsulated nanocarriers were successfully produced, and loading of doxorubicin was optimized to reflect the appropriate concentration desired for delivery in vivo (~6.9 mg IB/mg DOX).

Figure 12:
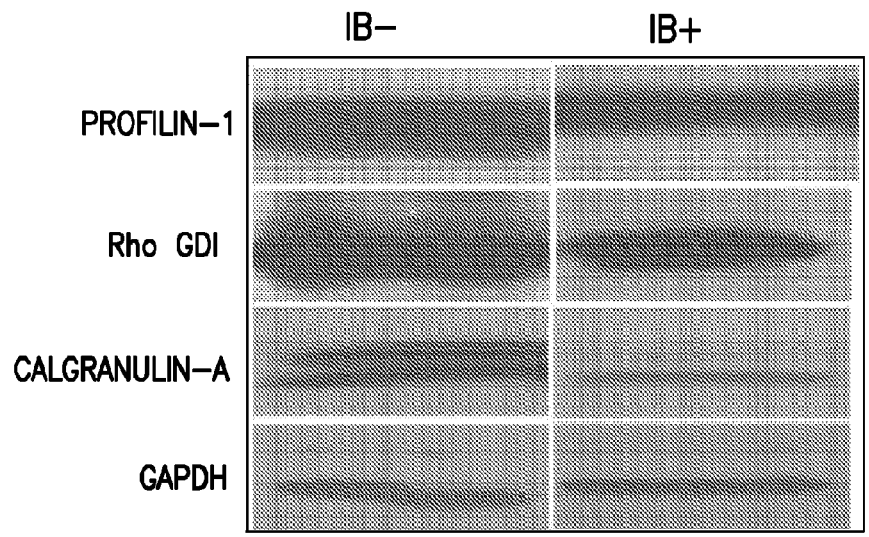
FIG. 12 shows a Western Blot analysis using 10 μg total protein obtained from Untreated-IB− (left) and nano-IB treated-IB+ (right) animals showing differences in cell proliferation and migration marker protein expression.

A proposed mechanism of action was determined through microarray analysis and in vitro studies. To this end, it was determined that IB appears to have acted by altering the arrangement of the cytoskeleton. Western blot analysis was used to measure the presence of markers for proteins as indicators of cell proliferation and migration. Western blot was performed on samples extracted from untreated and nano-IB treated rat brains. The blots showed marked differences in expression of cell proliferation and migration marker proteins between the two treatments. Nano-IB treated animals showed reduced expression of the cell proliferation and migration markers: Profilin-1 and Calgranulin-A, and of the GDP dissociation inhibitor-RhoGDI, when compared to the untreated animals (FIG. 12). Profilin-1 is known to promote binding to actin monomers, which along with Calgranulin-A are known to be involved in promoting cell proliferation and differentiation. RhoGDI prevents the dissociation of Guanosine diphosphate (GDP) in exchange for Guanosine triphosphate (GTP) which is needed to activate RhoA, a cell proliferation inhibitor.

The effects of Imipramine Blue on halting invasion in different cancer cell lines has also been evaluated, to determine whether the same mechanism of action applies. To this end, invasion assays have been run on multiple human and rat glioma cell lines; including RT2A, C6, F98, and U87 (results not shown).

Figure 13:
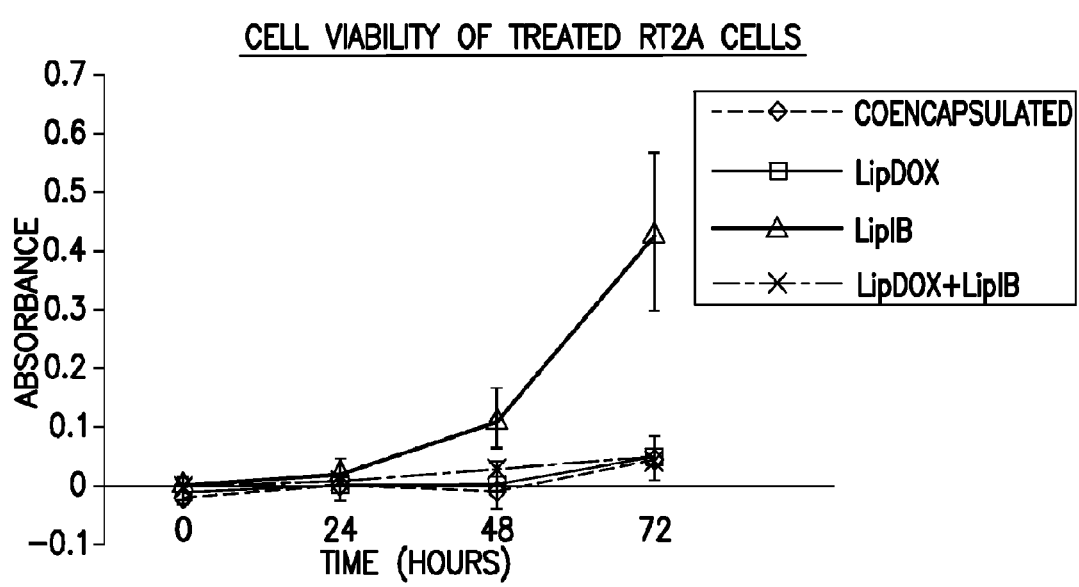
FIG. 13 is a chart showing cell viability as measured through an in vitro cell proliferation assay (cell viability as indicated through absorbance over time (hours)). Co-encapsulated IB+DOX was as cytotoxic as liposomal DOX alone or liposomal DOX in conjunction with liposomal IB. Liposomal IB (which has a method of action to halt cellular invasion rather than serving as a cytotoxic agent) served as a control.

In preparation for in vivo studies evaluating the effect of IB in combination with chemotherapeutics (e.g., doxorubicin), nanocarrier formulations loaded with both IB and doxorubicin were tested in vitro for their effect on cell viability. When formulating the coencapsulated liposomes, one goal was to determine whether it was possible to encapsulate a high enough concentration of each of the therapeutics, and also whether coencapsulation impacted potency of either component. The coencapsulated liposomes also offer a two-pronged approach to tumor therapy—anti-invasion and cytotoxicity—which produces better results than either treatment alone. The coencapsulated liposomes were found to be as cytotoxic as liposomal doxorubicin alone or liposomal doxorubicin (DOX) delivered in conjunction with liposomal IB as tested by an in vitro cell proliferation assay (the level of absorbance indicates the number of viable cells). Thus, the co-encapsulated liposomes encapsulated enough DOX for the doxorubicin to retain its potency (FIG. 13).

EXAMPLE 5

Imipramine Blue Increases Survival Time in RT2 Tumor-bearing Rats

Figure 14:
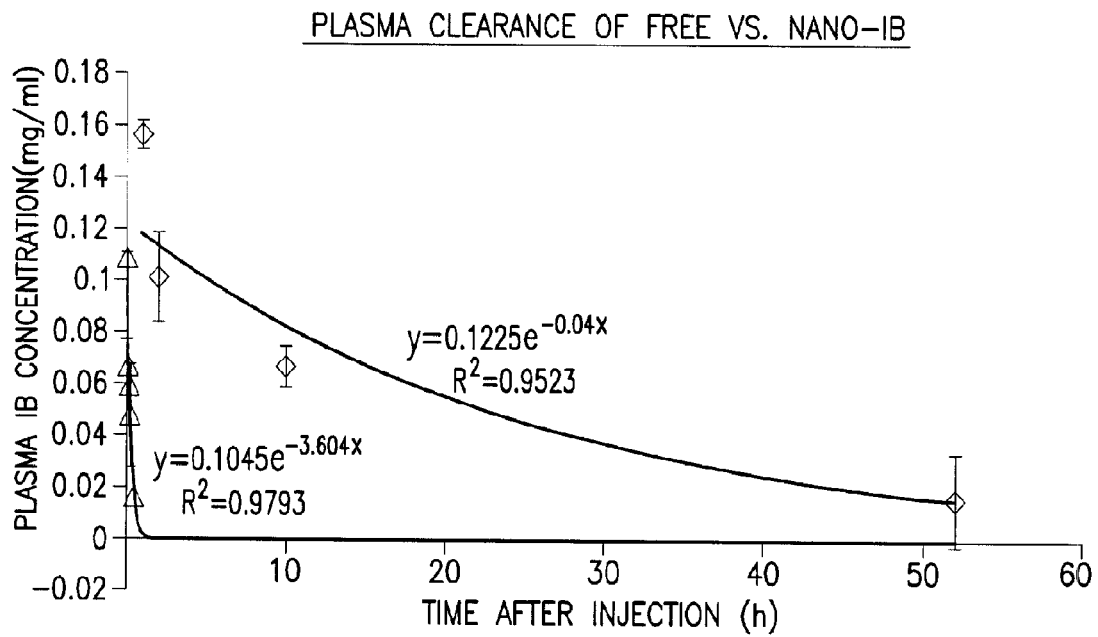
FIG. 14 is a chart showing the plasma clearance of free imipramine blue ("IB") versus nanoencapsulated imipramine blue ("Nano-IB"), in terms of plasma IB concentration (mg/ml) over time after injection (h).
Figure 15:
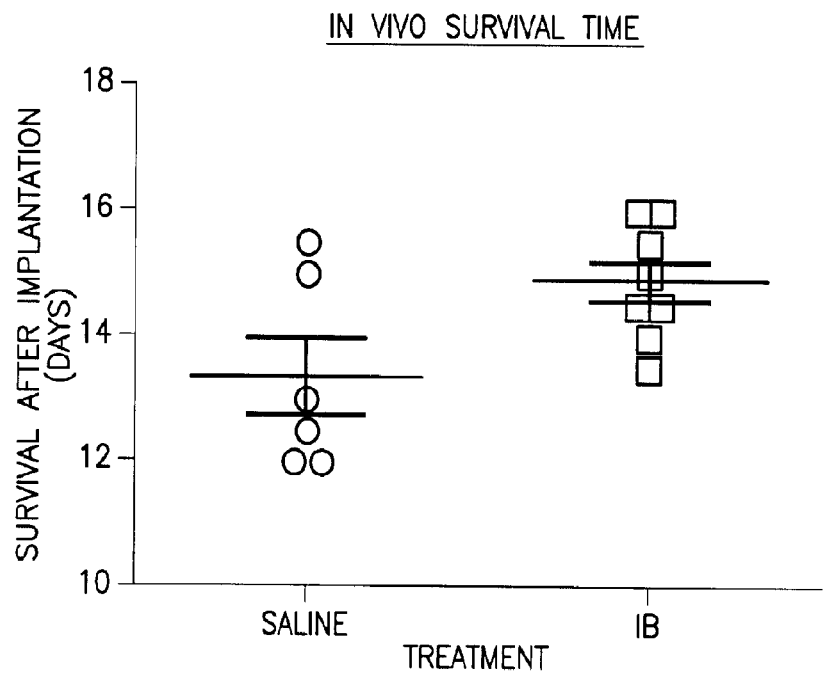
FIG. 15 is a chart showing the in vivo survival time after implantation (days) with treatment with saline control (saline) or imipramine blue ("IB").

To determine how Imipramine Blue (IB) changes survival time, RT2 glioma bearing rats were given Imipramine Blue liposomes (Nano-IB) allowed to survive until signs of morbidity were apparent. Animals were inoculated with tumor into the rear cortex via intracranial injection. On days 4 and 7 after inoculation, Nano-IB or saline was delivered via the tail vein. Delivery of Nano-IB yielded a 12% increase in survival time that was statistically significant (p=0.037) from saline control treated tumor bearing animals. Results are shown in FIG. 14.

EXAMPLE 6

Encapsulation of Imipramine Blue in Liposomes Increases Circulation Half-Life

Imipramine Blue liposomes were injected via the tail vein into adult male rats (non tumor-bearing). Blood samples were taken via the orbital cavity at different time points after drug administration, plasma separated and analyzed for IB content via absorbance readings on spectrophotometer. Measurements for free IB were taken over the course of 1 hour at which point readings were below detectable range and for Nano-IB readings were taken for 52 hours. Results are below with curves fit to the data. Half-life of IB once encapsulated was increased from 12 minutes to 18 hours yielding more time for tumor accumulation and less non-specific compartmentalization.

The following references related to various aspects of the working examples and/or to the background of the invention described herein. These references, and all other references cited herein, are hereby incorporated by reference for all purposes.

References

Karathanasis, E., et al. (2008) Biomaterials, 29(36):4815-22

Surawicz, T., et al. (1998) Brain tumor survival: Results from the National Cancer Database. *J. Neuro-Oncol.* 40:151-60.

Tonn, C., et al. (1999) Effect of synthetic matrix-metalloproteinase inhibitors on invasive capacity and proliferation of human malignant gliomas in vitro, *Int. J. Cancer,* 80:764-72.

K. Singla, A. Garg, D. Aggarwal, Paclitaxel and its formulations, Int. J. Pharm. 235 (2002) 179-192.

From this description the essential characteristics of the invention can be readily ascertained and, without departing from the spirit and scope thereof, the invention can be adapted to various usages. Changes in form and substitution of equivalents are contemplated as circumstances may suggest or render expedient, and although specific terms have been employed herein, they are intended in a descriptive sense and not for purposes of limitation.

The invention claimed is:

1. A composition for treating tumors in a patient, comprising unilamellar liposomes, of a size of less than 200 nanometers as assessed by dynamic light scattering and containing a therapeutic amount of imipramine blue, or a pharmaceutically-acceptable salt thereof, in a pharmaceutically-acceptable carrier for intraveneous administration, wherein the liposomes comprise cholesterol and chemically pure phospholipids that are essentially neutral and contain saturated fatty acids of between 16 and 18 carbon atoms.

2. The composition of claim 1, wherein the liposomes have a size of from about 50 to about 160 nanometers.

3. The composition of claim 1, wherein the phospholipids are synthetic phospholipids.

4. The composition of claim 1, wherein the phospholipids comprise distearoylphosphatidyl choline.

5. The composition of claim 1, wherein the phospholipids comprise a pegylated phospholipid.

6. The composition of claim 1, wherein the phospholipids comprise DSPC, DSPE-PEG, and cholesterol.

7. The composition of claim 6, wherein the ratio of DSPC/DSPE-PEG/cholesterol is about 85%/about 5%/about 10%.

8. The composition of claim 1, further comprising an antitumor agent other than imipramine blue.

* * * * *